(12) United States Patent
Kamer

(10) Patent No.: US 11,766,065 B2
(45) Date of Patent: Sep. 26, 2023

(54) SYSTEM AND METHOD FOR PREPARING MIXTURE OF GROUND SUBSTANCES DISPENSED IN ONE OR MORE RECEPTACLES

(71) Applicant: Sason Kamer, Tel Aviv (IL)

(72) Inventor: Sason Kamer, Tel Aviv (IL)

(*) Notice: Subject to any disclaimer, the term of this patent is extended or adjusted under 35 U.S.C. 154(b) by 339 days.

(21) Appl. No.: 16/878,835

(22) Filed: May 20, 2020

(65) Prior Publication Data
US 2020/0367549 A1 Nov. 26, 2020

Related U.S. Application Data

(60) Provisional application No. 62/851,114, filed on May 22, 2019.

(51) Int. Cl.
A24B 3/08 (2006.01)
B02C 23/10 (2006.01)
(Continued)

(52) U.S. Cl.
CPC ............... *A24B 3/08* (2013.01); *A24C 5/002* (2013.01); *A24C 5/06* (2013.01); *A24C 5/3424* (2013.01); *A24D 1/18* (2013.01); *A61K 36/185* (2013.01); *B01F 23/69* (2022.01); *B01F 23/71* (2022.01); *B01F 23/713* (2022.01);
(Continued)

(58) Field of Classification Search
CPC .. A24B 3/08; A24C 5/002; A24C 5/06; A24C 5/42; A24C 5/3424; A24D 1/18; A61K 36/185; B01F 23/69; B01F 23/71; B01F 23/713; B01F 35/188; B01F 35/2117; B01F 35/832; B02C 18/142; B02C 23/10;
(Continued)

(56) References Cited

U.S. PATENT DOCUMENTS

| 595,474 A | * | 12/1897 | Hayden et al. | 131/171 |
| 2011/0011411 A1 | * | 1/2011 | Accordino | A24C 5/00 |
| | | | | 131/70 |

(Continued)

FOREIGN PATENT DOCUMENTS

| CN | 107890925 A | * | 4/2018 | ............. B01D 46/10 |
| GB | 2356797 A | * | 6/2001 | ............... A24C 5/40 |

OTHER PUBLICATIONS

CN 107890925 A—machine translation (Year: 2018).*

*Primary Examiner* — Michael J Felton
*Assistant Examiner* — Ronnie Kirby Jordan
(74) *Attorney, Agent, or Firm* — LAW OFFICES OF STEVEN W. WEINRIEB

(57) ABSTRACT

An apparatus and method for automatically preparing a mixture of particles of two or more substances such as but not limited to raw tobacco and raw medical cannabis flowers in one or more receptacle where the mixture proportion is predefined, is disclosed. The apparatus of the invention can be used for mixing any types of herbal substances. Moreover, the apparatus of the invention can be used for mixing one or more kinds of the same substance, for example mixing two or more kinds of marijuana strains. The apparatus includes one or more compartments for inserting each of the substances separately. In some variations of the present invention the size of at least one of the compartments is smaller for predefined smaller quantities of raw herbal material for example, a single marijuana flower.

25 Claims, 8 Drawing Sheets

(51) Int. Cl.
*B01F 23/70* (2022.01)
*B01F 35/21* (2022.01)
*B01F 23/60* (2022.01)
*B01F 35/83* (2022.01)
*A24C 5/00* (2020.01)
*A24C 5/06* (2006.01)
*A24C 5/34* (2006.01)
*A24D 1/18* (2006.01)
*A61K 36/185* (2006.01)
*B02C 18/14* (2006.01)
*B02C 25/00* (2006.01)
*B01F 35/00* (2022.01)

(52) U.S. Cl.
CPC ........ *B01F 35/188* (2022.01); *B01F 35/2117* (2022.01); *B01F 35/832* (2022.01); *B02C 18/142* (2013.01); *B02C 23/10* (2013.01); *B02C 25/00* (2013.01)

(58) Field of Classification Search
CPC .. B02C 25/00; A47J 42/26; A47J 42/30; A47J 42/36; A47J 42/40
USPC .......................................................... 131/70
See application file for complete search history.

(56) References Cited

U.S. PATENT DOCUMENTS

| | | |
|---|---|---|
| 2014/0261471 A1* | 9/2014 | Ruzycky .................. A24C 5/02 131/108 |
| 2015/0298135 A1 | 10/2015 | Spielman |
| 2017/0713898 * | 3/2017 | Lanier ..................... A47J 31/42 |
| 2017/0368554 A1 | 12/2017 | Nichols |
| 2018/0035711 A1* | 2/2018 | Rayson .................... A24F 15/10 |
| 2018/0055288 A1* | 3/2018 | Rose et al. .............. A47J 42/44 |

* cited by examiner

SYSTEM AND METHOD FOR PREPARING MIXTURE OF GROUND SUBSTANCES DISPENSED IN ONE OR MORE RECEPTACLES

CROSS-REFERENCE TO RELATED APPLICATIONS

This patent application is a non-provisional conversion of U.S. Provisional Patent Application No. 62/851,114 filed on May 22, 2019, the priority benefits of which are hereby claimed.

FIELD OF THE INVENTION

The present invention relates to medical cannabis, in particular in the field of preparing mixed cannabis and tobacco joints.

BACKGROUND OF THE INVENTION

Many kinds of devices for making cannabis cones/joints are known in the art, however, there is a need for an apparatus that does all of the functions including, the preparation, filling and packaging measured amounts of grinded cannabis and tobacco mixed together inside a tube or a rolled paper cones. Such an apparatus will save valuable time for example for helping people with motor difficulties or mobility problems that consume medical cannabis, and will also improve their quality of life. The aggregated time of repeatedly performing the process of grinding the cannabis and the tobacco, mixing them, and filling the paper cones with the mixed substances takes relatively a long time for a user to perform. Moreover, the user is unable to accurately monitor and control the quantity ratio between the tobacco and the cannabis substances in each joint.

Joints that are mixed with both cannabis and tobacco are also known as a "spliff" in some countries. The reason people choose to mix cannabis and tobacco vary greatly, but most people do so for the unique effects it produces. Most users who mix cannabis and tobacco report experiencing a mellow, relaxing and more controllable "high" than if they were to smoke pure cannabis. Other users mix cannabis and tobacco for more practical reasons. For example, many people find that adding a little touch of tobacco helps them achieve an even, stronger burn in a joint or blunt.

Devices known in the art that a joint smoker uses in the process of preparing a joint are divided to several types of devices, depending on the specific step(s) in the process of making a joint:

Accommodations: There is a variety of accommodation products that provide optimal conditions for the preservation of cannabis and tobacco. Such devices also keep the substances (the cannabis or the tobacco) fresh.

Grinding: the grinding of the cannabis and the tobacco is typically done by using products known as Grinders. Some of the grinders also include storage, filtration and removal of the raw materials. Some grinders use blades and some use the shape of teeth inside the inner compartment where the cannabis is stored. Some of these grinders are electronic and others are manually used.

Dispensers: Some of the devices perform the operation of dispensing the grinded cannabis into a rolled paper cone or a tube.

Measurement and monitoring: as the Internet Of Things (IOT) has advanced, more and more measuring instruments have emerged, including IOT devices for cannabis consumption. Further, as the IOT devices emerged, so did the need of users to monitor and control their substances consumption.

US20170368554 discloses an integrated grinding and storage system for optimizing and enhancing plant performance for plant-based medical therapies and related uses of cannabis including an apparatus for grinding that includes a head operable to be removably attached to a receptacle or container. The head includes a magnet, an upper, inner grinding element, a lower grinding element, a shaft, and a neck sleeve. The upper, inner grinding element is in communication with the lower grinding element within the head. The grinding elements are operable to rotate relative to each other. The shaft extends between the upper and lower sections and magnetically couples with the grinding elements and orients them in relation to one another. The head may be manually or electrically activated.

US20150298135 describes a tobacco grinding apparatus having a grinding chamber, including a grinder mechanism, for grinding a grindable material. An intermediate chamber is used for receiving ground material which has been ground by the grinder mechanism. The intermediate chamber includes an aperture for delivery of ground material from the intermediate chamber to a selected delivery location. A plurality of receptacles for receiving ground material, ground by the grinder and contained within the intermediate chamber. each one of the plurality of receptacles defining a separate receptacle volume, each of the separate receptacle volumes each being separately, selectively alignable with the aperture of the intermediate chamber to thereby selectively receive ground material dispensed from the intermediate chamber.

However, all of the abovementioned art disclose products which perform only part of the Joint preparation process. Further, the disclosed prior art do not provide a tool to accurately monitor and control the quantity ratio between the tobacco and the cannabis substances in each joint.

One object of the present invention is to provide all of the above mentioned steps in a single apparatus for the joint preparation process.

Yet another object of the present invention is to provide an apparatus that can mix ground and/or filtered tobacco or other herbal based material with ground and filtered cannabis and dispense the mixed substances particles in one or more rolled paper cones or a tubes.

Yet another object of the present invention is to provide an apparatus that can mix two different types or more of ground and filtered cannabis and dispense the mixed substances particles in one or more rolled paper cones or a tubes.

Yet another object of the present invention is to provide an apparatus that mixes cannabis with tobacco in a tube or rolled cone where the user can control the quantity proportion between the cannabis and the tobacco.

Yet another object of the present invention is to provide an IOT apparatus that can monitor, track, learn about user cannabis smoking consumption habits and adapting the cannabis and tobacco proportion according to the user preferences.

SUMMARY OF THE INVENTION

The present invention relates to medical cannabis, in particular in the field of preparing joints of mixed cannabis and tobacco.

In accordance with one aspect of the present invention there is provided a method for preparing mixture of two or more substances in one or more receptacle, where the mixture proportion between the substances can be determined. The method comprises the steps of inserting the two substances into two or more compartments. The proportion mixture and the quantity of each of the two substances is determined. From each of the compartments a predetermined amount of substance according to the mixture proportion quantity determination is released to a mixer. The released substances are measured, grinded and mixed thereafter. The one or more receptacle is filled with mixed substances.

In another aspect of the present invention there is provided an apparatus for preparing automatically a mixture of particles of two or more substances such as but not limited to raw tobacco and raw medical cannabis flowers in one or more receptacle where the mixture proportion is predefined. The apparatus of the invention can be used for mixing any types of herbal substances. Moreover, the apparatus of the invention can be used for mixing one or more kinds of the same substance, for example mixing two or more kinds of marijuana strains. The apparatus includes one or more compartments for inserting each of the substances separately. In some variations of the present invention the size of at least one of the compartments is smaller for predefined smaller quantities of raw herbal material for example, a single Marijuana flower. In other variations of the present invention the one or more compartments are preadjustable. The apparatus includes also one or more grinders with inlet and outlet. The grinders having chopping and breaking elements for chopping and breaking the substances that passes through the grinder inlet. One or more digital scales for measuring the ground substances that passes through outlet of the one or more grinders are measured separately by the one or more digital scale. A controller receives the measurements of the scale(s) and instruct for defining the mixer proportion between the mixed substances. One or more mixer are used for mixing the at least two substances particles. One or more motors and motor driver(s) can be used for automatically activating the mixer(s) and the grinder(s) by the controller. The mixed ground substances according to the predefined mix proportion are passed to the one or more receptacles.

BRIEF DESCRIPTION OF THE DRAWINGS

The invention may be understood upon reading of the following detailed description of non-limiting exemplary embodiments thereof, with reference to the following drawings, in which.

DETAILED DESCRIPTION OF EMBODIMENTS OF THE INVENTION

The following detailed description of the invention refers to the accompanying drawings referred to above. Dimensions of components and features shown in the figures are chosen for convenience or clarity of presentation and are not necessarily shown to scale. Wherever possible, the same reference numbers will be used throughout the drawings and the following description to refer to the same and like parts.

In accordance with the present invention there is provided a system and method for preparing a joint or a tube with a mixture of medical cannabis and tobacco where the amount of cannabis and tobacco in the joint or the tube can be automatically controlled and monitored. The joint for example, could be a mixture of the tobacco and cannabis inserted inside of a rolled paper forming a shape of a cone. The prepared joints can be afterwards packed in a package.

Figure 1:
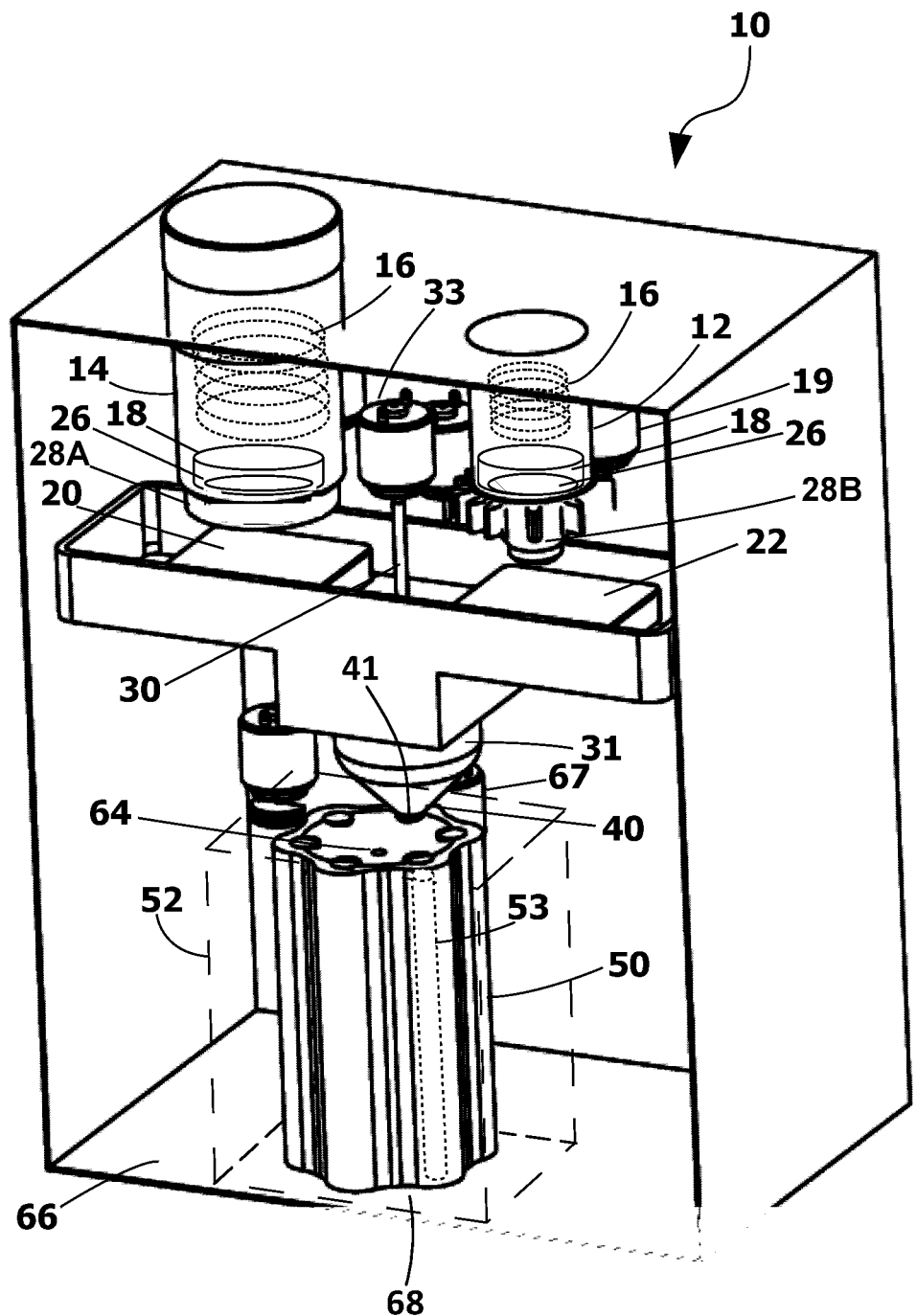
FIG. 1 is a perspective front view illustrating schematically a system for preparing mixed cannabis and tobacco joint in accordance with one embodiment of the present invention.

Referring to FIG. 1 there is shown a perspective front view illustrating an apparatus 10 for preparing a joint or a tube with a mix of cannabis and tobacco in accordance with a preferred embodiment of the present invention. Apparatus 10 includes two compartments 12 and 14. Compartment 12 is used for storing the raw medical cannabis flowers and compartment 14 is used for storing the raw tobacco leaves. Compartments 12 and 14 may include any suitable compression means for compressing the substances inside compartments 12 and/or 14 for example a mechanical substance compressor using one or more springs 16. Apparatus 10 further includes one or more grinders 18 typically having chopping and breaking elements, not shown in FIG. 1, for chopping and breaking the raw substances. The grinder(s) 18 can be operated manually while in other embodiments of the present invention one or more actuators such as but not limited to electric motor 19 are provided to assist with the grinding operation. Apparatus 10 further includes one or more scales preferably digital scale(s). In FIG. 1 there are illustrated two digital scales 20 and 22. The grinder(s) may further include one or more filters 26 which only the ground substances particles which are small enough pass through the filter(s) to grinding chamber 28A and 28B respectively. The grindings chambers 28A and 28B have an outlet that may have a funneled shaped configuration. The ground substances pass through outlet of the chambers 28A and 28B to the digital scales 20 and 22 respectively.

According to the present invention the grinding operation can be operated automatically and for predetermine time thus in associate with the measurements of the digital scales 20, 22 and a controller 100 (shown in FIG. 2), the apparatus of the present invention can provide mixed cannabis and tobacco substances with predetermined quantity proportion between them. The controller 100, instruct to operate the grinders for a predetermine time then the ground substances are measured separately. The measurement readings are sent to the controller for processing the measurement results. According to the measurement results the controller instructs the grinder how long and when to operate in order to get the desired quantity proportion between the two substances. It should be noted that this is an exemplary embodiment and in some embodiments the apparatus of the invention can operate for preparing a proportion mix of more than two substances. Furthermore, in some embodiments of the present invention the apparatus of the invention may include only one digital scale electrically connected to the controller, in this case the ground substances are passed to the digital scale one at a time, meaning that the first ground substance is being scaled and after the controller receives the measurement reading, the weight of the second ground substance is measured. In some embodiments of the present invention chamber outlets can be automatically closed or opened for example by using a controlled motor driving, a controller, motor and a surface connected to the motor where the surface is configured to close or open the outlets according to the controller electric command signal. It should be noted that other means and configurations can be used to automatically close or open the outlets. When the outlet for example, is opened for a predetermine time a certain amount of ground cannabis and/or tobacco is falling through the outlet to one or more digital scales that measure the weight of the quantity of the ground cannabis and/or the tobacco. When and for how long the outlets are opened or closed can be determined by the controller. The measured weights can then be displayed on a display for user's purposes.

In other embodiments of the present invention the measured quantities can be digitally stored on an internal or external memory for further analysis by utilizing any suitable processing means known in the art. In some embodiments of the present invention apparatus 10 may include two digital scales 20 and 22 for measuring each substance while in other embodiments of the present invention apparatus 10 may include only one digital scale and the weight measurements of each quantified substance are done in a successive manner. In other embodiments of the present invention apparatus 10 may include instead of the two compartments 12 and 14 only one compartment and only one digital scale where the tobacco and the cannabis substances are inserted in the apparatus compartment successively and the grinding and weight measurements are done separately. Apparatus 10 further includes a mixer 30 having a mixer chamber 31 for receiving the weighted tobacco and cannabis substances and mixing them together. The mixer is connected to a motor 33 controlled by the controller. In some embodiments of the present invention a suitable sweeper mechanism is provided for sweeping the measured ground substances to mixer 30. The mixed substances are then passes to a funnel 40 having an inlet and outlet. The funnel 40 is configured for inserting the mixed tobacco and cannabis to an empty cone or tube which can be centrally aligned with the funnel outlet 41. In the preferred embodiment of the present invention apparatus 10 may include cones/tubes cartridge 50 and a cartridge housing 52. One or more tubes and/or cones 53 or any other suitable storing means are stored on the cartridge; preferably each cartridge 50 may store a pack of up to ten cones/tubes. The cartridge 50 is constructed in such a way that the cones and/or tubes are positioned perpendicular to the apparatus bottom surface 66 and one at a time cone or tube 53 in the cartridge 50 is aligned with the funnel outlet for receiving the mixed substances. Cartridge 50 is configured to rotate around pivot 64, positioned perpendicular to apparatus bottom surface 66. Cone(s) and/or tube(s) 53 are positioned in the cartridge substantially parallel to pivot 64 and in even distances from pivot 64 in such a way that each tube or cone can be aligned with the funnel outlet when rotating the cartridge around pivot 64. Whenever cone or a tube 53 is filled with the mixed substances, cartridge 50 rotates to the next cone or tube to be filled with the mixed substances. In one embodiment of the present invention cartridge 50 is rotated manually, while in other embodiments of the present invention cartridge 50 may rotates automatically with electric motor 67 and with a predetermined electric signal command sent from the controller. Pivot 64 can be attached to cartridge bottom surface 68 and can be actuated by the motor 67 and a controlled driver. In some embodiments of the present invention when the tubes 53 are filled with the mixed substances, a suitable sealing cap can be used for sealing the filled tubes for preserving the mixture for future uses. In some embodiments of the present invention the tubes can be replaced by a tube shaped canister that can be sealed for the preservation of the mixture for future use.

Figure 2:
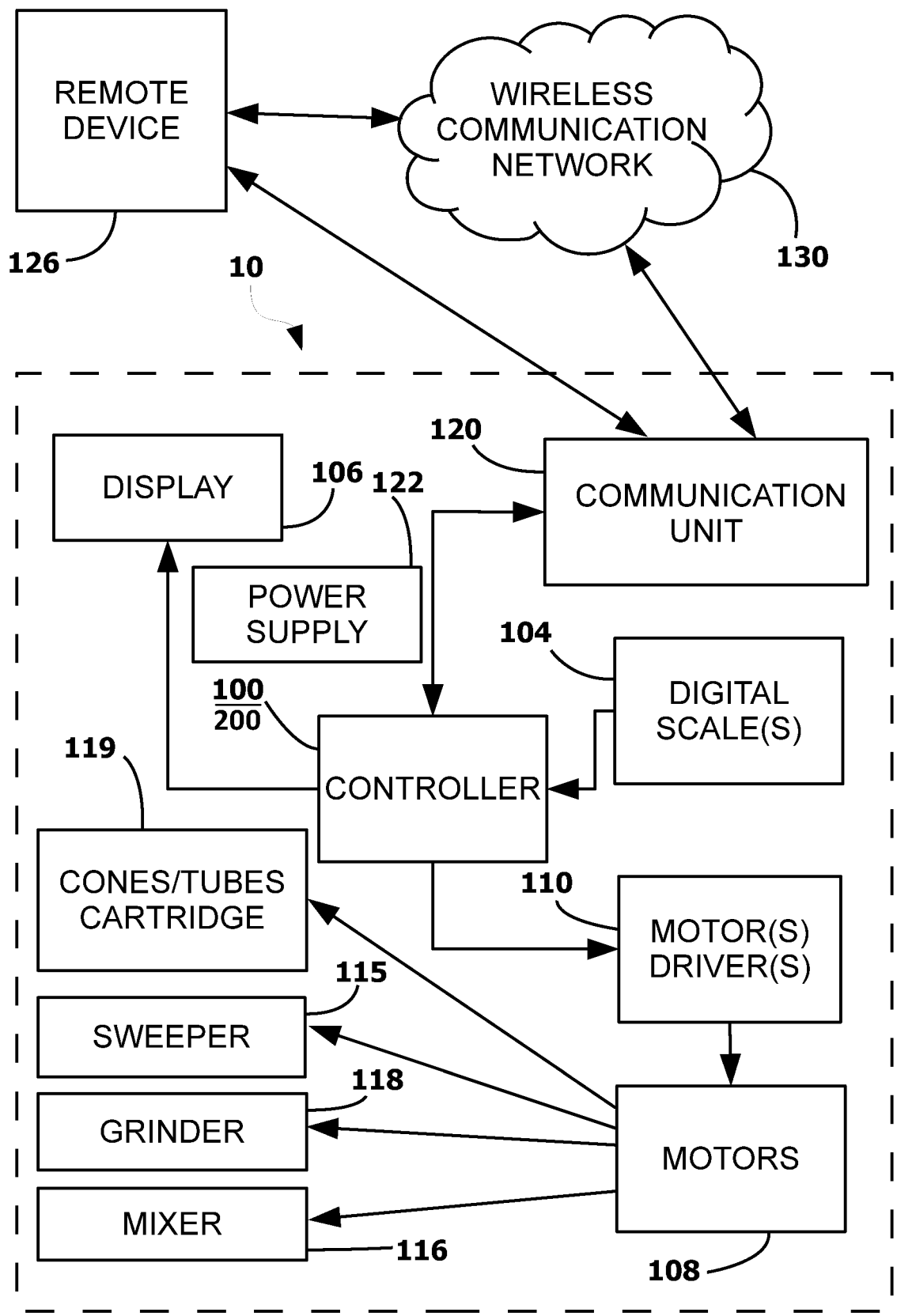
FIG. 2 is a schematic block diagram of a system for preparing mixed cannabis and tobacco joint in accordance with some embodiments of the present invention.

Referring now also to FIG. 2 in accordance with some embodiments of the present invention apparatus 10 includes controller 100 which may include also an internal memory 102. The apparatus also includes digital scales 104 for the purpose that mentioned above. The readings of the scales 104 are fed to one or more of the controller input(s) for data processing. Apparatus 10 further includes a display 106 electrically connected to controller 100. The display 106 can display information such as but not limited to the substances weight, the proportion between the grinded cannabis and the grinded tobacco in the tubes/cones, etc. The apparatus 10 further includes one or more actuators such as but not limited to electric motors 108 driven by one or more motor drivers 110 which receive commands from controller 100. Apparatus 10 includes a mixer 116 for mixing the two substances, one or more grinders 118 for grinding the two substances, a sweeper 115 for sweeping the two grinded substances to the mixer 116. Each motor 108 can be used for different purposes in the apparatus 10 for example, for rotating the cones/tubes cartridge 50 around the cartridge pivot 64, grinding the two substances, mixing the two substances, etc. apparatus 10 further includes a power supply 122 for powering the electronic components in the apparatus 10.

In some embodiments of the present invention apparatus 10 may include a communication unit 120 which can communicate with one or more remote digital devices 126 such as but not limited to a Smart phones, PCs, tablets web servers etc. The remote device 126 may include one or more applications which can receive and/or send information from/to apparatus 10 through communication unit 120. Remote device 126 may include a database and one or more algorithms to analyze the readings from the digital scales 104 and to provide on the remote device useful information for example about the user cannabis/tobacco consumption habits based on the information received from apparatus 10 through communication unit 120.

Communication unit 120 may include WIFI, BLUETOOTH® or any other suitable communication methods known in the art for communicating between communication unit 120 and remote device 126 for example through a wireless communication network 130 such as but not limited to the Internet. Remote device 126 can wirelessly control the operations of apparatus 10. For example, to determine the desired quantity pupation of the mixed grinded cannabis and tobacco a user wants to prepare to be filled in a tube/cone. Remote device 126 may further include graphic user interface with virtual control buttons for the user to send control commands to the apparatus 10. The commands could be for example, setting the desired proportion between cannabis and tobacco to be in a tube and/or in a rolled paper cone. Another command example could be setting the desired size of the tube or cone.

In some embodiments of the present invention apparatus 10 one or more parts of the apparatus 10 can be disassembled by the user for cleaning and replacement purposes. For example, the grinder 118, the compartments 12,14 the scale 104 and the mixer 116 parts can be disassembled for cleaning and replacing purposes.

In some embodiments of the present invention apparatus 10 may also include an odor filter.

Figure 3:
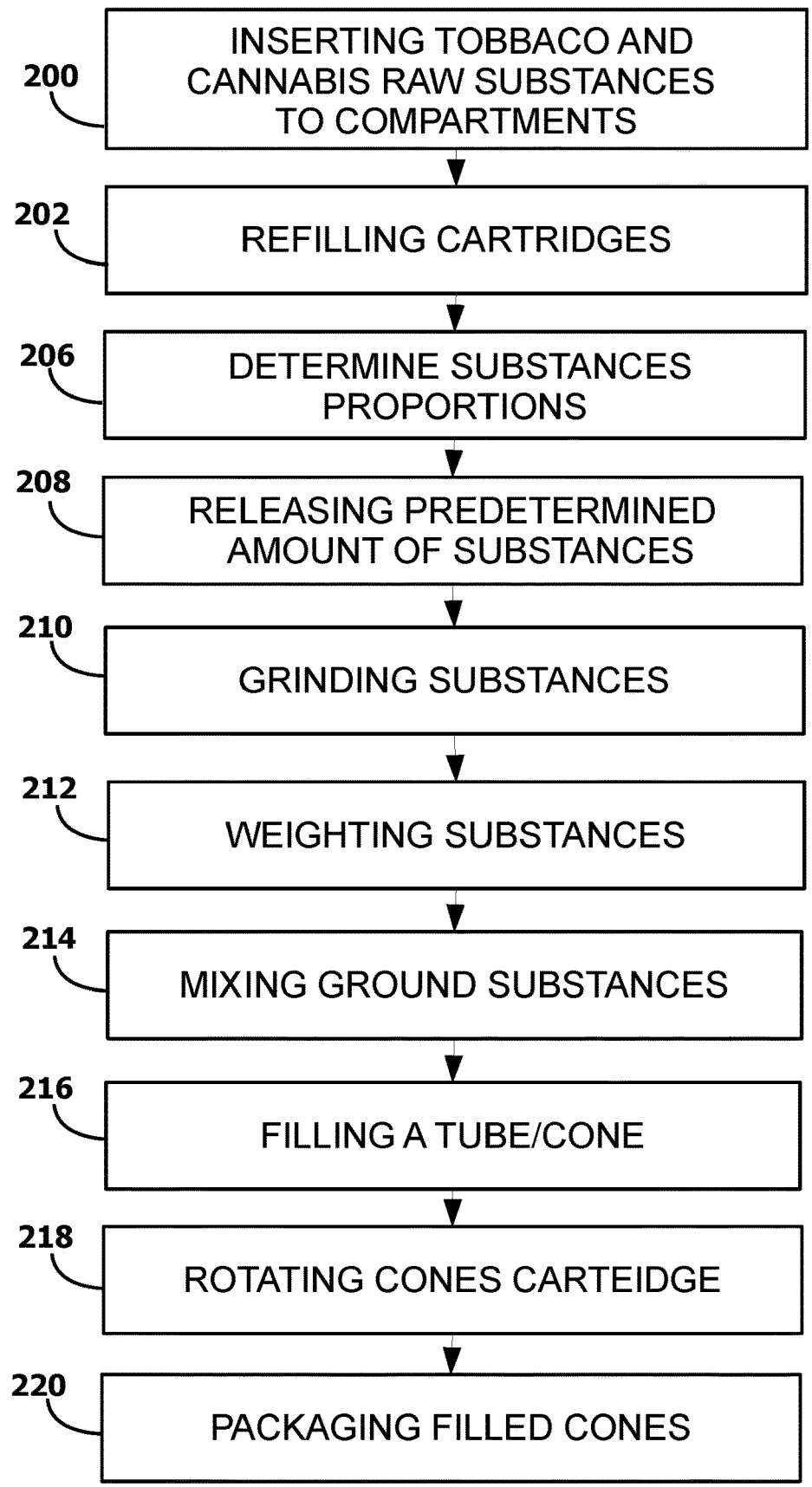
FIG. 3 is a flowchart describing a method for preparing mixed cannabis and tobacco joint in accordance with some embodiments of the present invention.

Referring now also to FIG. 3 there is shown a flowchart describing an exemplary method for preparing mixed cannabis and tobacco joint in accordance with some embodiments of the present invention. In step 200, a user inserts raw tobacco substance to compartment 14 and inserts raw cannabis substance to compartment 12. In step 202, the user pulls out from the apparatus 10 the cones cartridge 50 and refills the cartridge with empty paper cones or tubes and inserts back the cartridge to the apparatus 10. In step 202, one of the empty cone or tube in cartridge 50 is further aligned with the funnel outlet 41. In step 206, the user sends instruction commands to apparatus 10 such as but not limited to, instructions for determining the proportion quantity of the cannabis and tobacco that will be dispensed in the end of the process in the tube or the rolled paper cone. Another instruction for example is to determine the size of the joint etc. In step 208, predetermines amount of raw substances are released to grinders 118. In step 210, grinding and filtering the released substances. In step 212, each grinded substance is weighted by one or more digital scales 104 or any other suitable weight measuring means known in the art. In some embodiments of the present invention the measured results can be displayed on display 106 or can be sent to remote device 126 through communication unit 120. The measured result can be further processed for analyzing user consumption behavior. In some embodiments of the present invention a suitable sweeping means 115 is used to sweep the weighted substances to mixing compartment of mixer 116. In step 214, both grinded substances are mixed. In step 216, filling the tube or cone with the mixed substances. In step 218, cartridge 50 is rotated such that the next tube or rolled cone paper will be aligned with the center of funnel outlet 41. The procedure of steps 208 until 218 is repeatedly started over and over again until all of the cones/tubes in the cartridge 119 are filled or until the user decides to end the filling steps. In step 220, the user pulls out the cartridge 50 with the filled cones from the cartridge housing 52 in apparatus 10 and the user can now manually pull out from the cartridge 50 the filled rolled paper or tube (joint) for use or storing in a suitable package to retain freshness.

Figure 4:
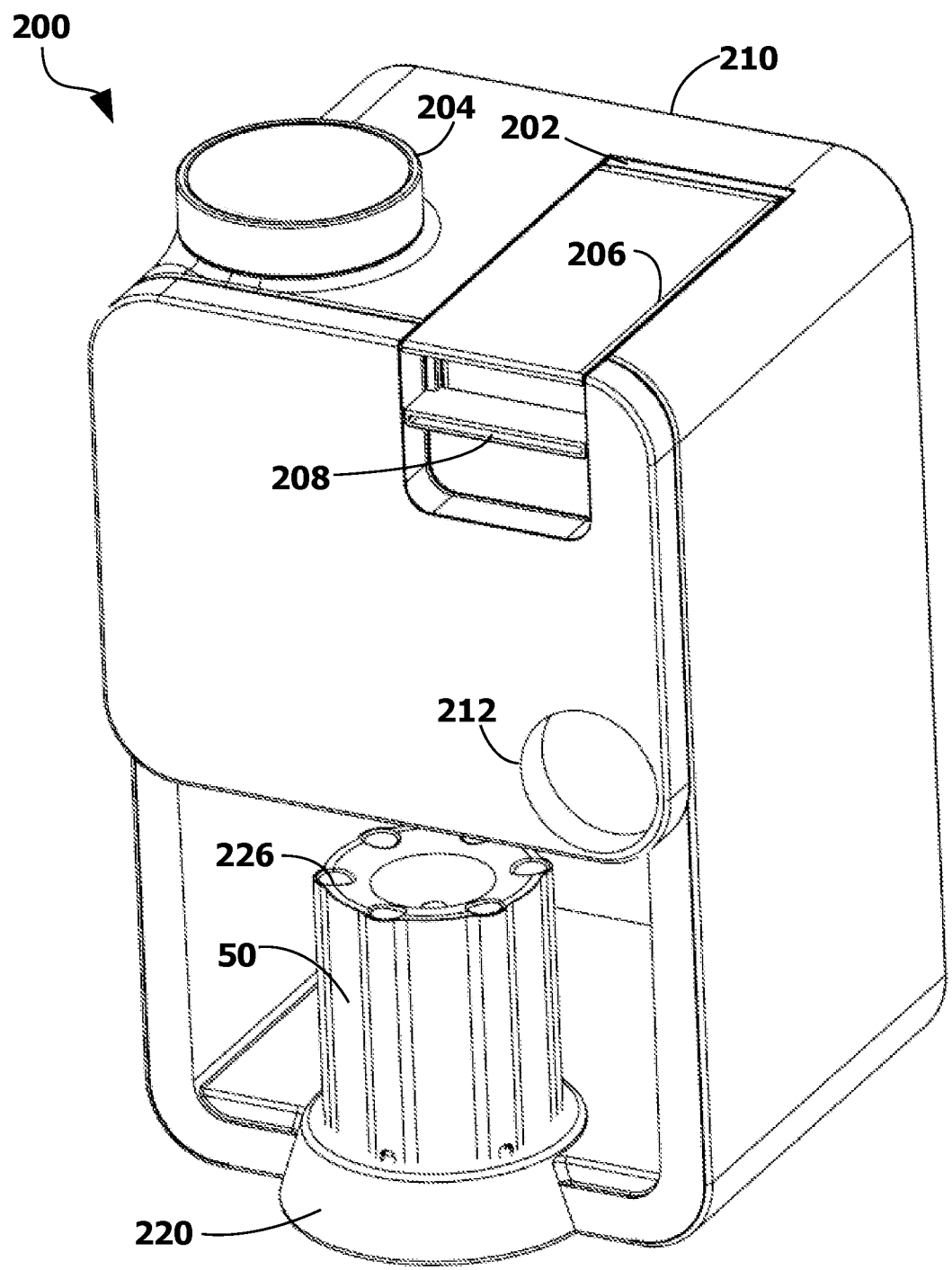
FIG. 4 is a perspective front view of an apparatus for preparing mixed cannabis and tobacco joint in accordance with another embodiment of the present invention with a rotatable cartridge for caring cones to receive mixed ground substances.

Referring to FIG. 4 there is shown an apparatus 200 that includes an apparatus enclosure 202. The apparatus further includes two covers, 204 and 206. Each of them covers the inlets of internal compartments inside the apparatus from which tobacco or cannabis substances can be inserted to the compartments. One of the compartments is used for storing cannabis substance and the second compartment is used for storing tobacco substance, cannabis substance or mix of cannabis and tobacco substances. Each of the covers 204 and 206 can be protected by a suitable electronic or electromagnetic lock that prevents the opening of the covers 204 and 206 by unauthorized persons. The apparatus may also include one or more suitable sensors that identifies when one or both of the covers 204 and 206 is opened. Cover 204 can be opened after the respective electric lock is in the open position. The cover 204 can be opened for example by rotating the cover several times counterclockwise or in other embodiment pulling the cover upward. Referring also to FIG. 6 cover 206 is shown in open position. The cover can be opened by pulling manually the cover 206 by a gripping handle 208 upwards in respect to the cover rotating axis 210 positioned in one end of the cover 202. Apparatus 200 further includes a rotatable knob 212 that can be used for controlling the electric functions of the apparatus 200. In some, embodiments of the invention the rotatable knob 212 may includes a screen such as but not limited to an organic light-emitting diode (OLED) screen 214 for displaying for example the user's chosen apparatus function to be executed or for displaying the readings of one or more sensors in the apparatus 200. The OLED 214 is shown schematically in FIG. 5.

For example, with the rotatable knob 212 the user can also adjusts the desired amount of substance(s) from each of the internal compartment that is going to be used by the apparatus 200 for further processing steps such as but not limited to grinding, mixing, weight scaling and etc. The user may also use rotatable knob 212 for start or stop actions, for configuration settings such as but not limited to determine the shape and size of the cones that receive the mixed and grounded substances. The rotatable knob 212 may also configure to navigate between menus of the apparatus 200. The rotatable knob display 214 may display warnings about the apparatus mechanical, electrical and software faults that may occur.

Figure 5:
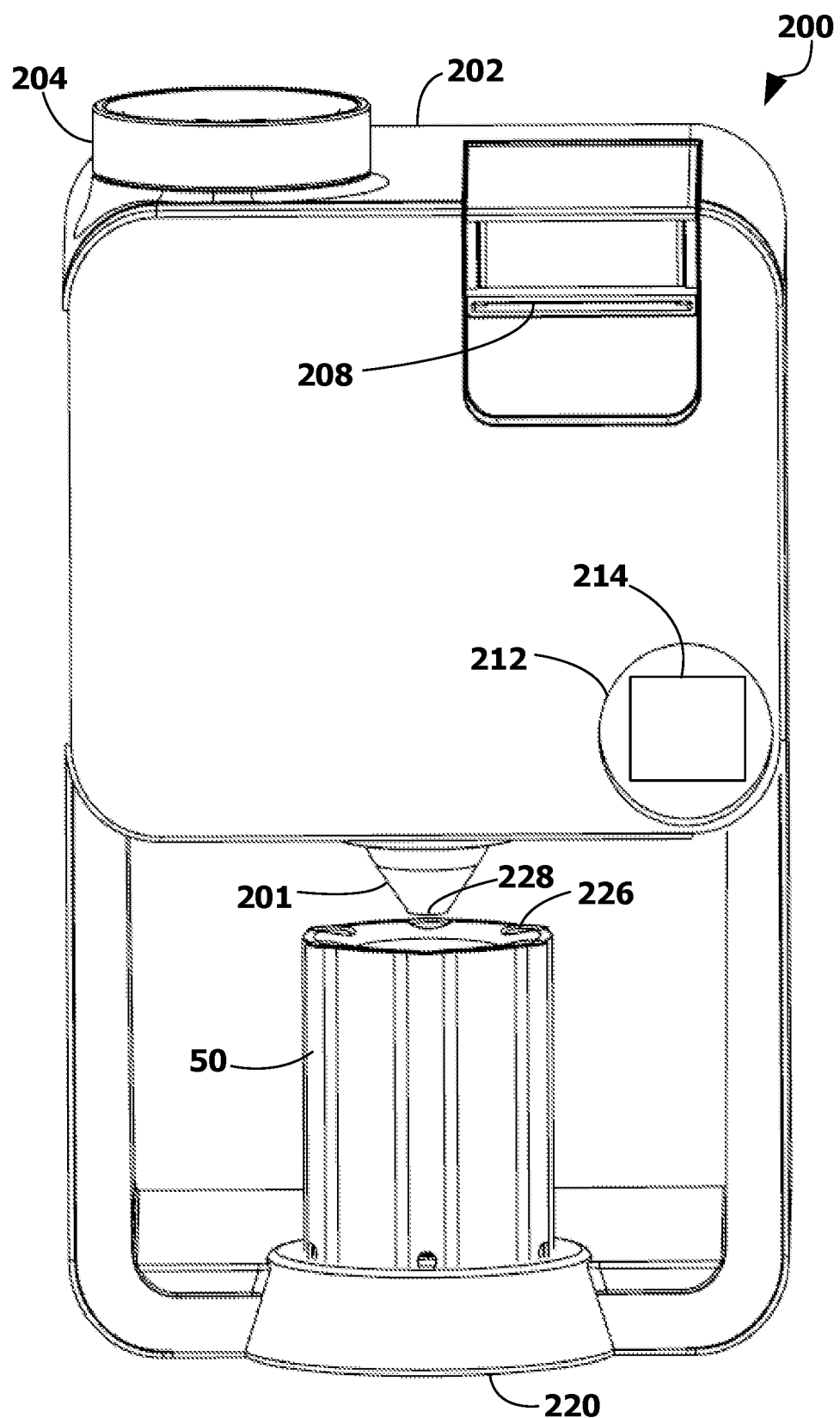
FIG. 5 is a front view of the apparatus for preparing mixed cannabis and tobacco joint as shown in FIG. 4.
Figure 6:
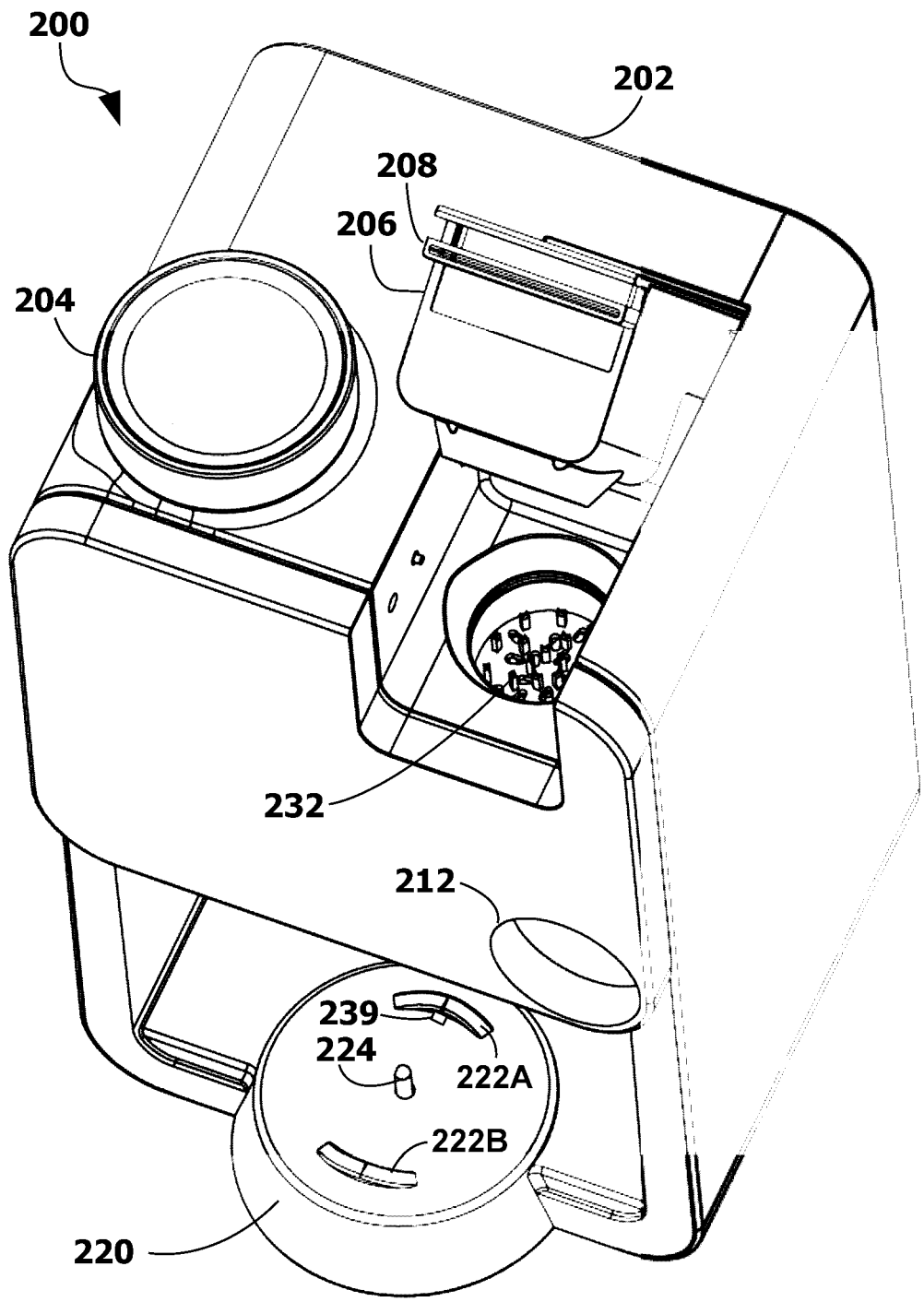
FIG. 6 is a front upper view of the apparatus for preparing mixed cannabis and tobacco joint as shown in FIG. 4 without the rotatable cartridge.

Referring to FIGS. 4 to 6 apparatus 200 further includes a funnel 201, the cones/tubes cartridge 50 and a cartridge stand 220. The cartridge stand 220 includes cone/tube elevation means 222A and 222B. The funnel 201 is configured for inserting the mixed tobacco and cannabis to an empty cone or tube which is centrally aligned with the funnel outlet 228. In the center of the cartridge stand 220 disposed a hole through which a rotating pivot 224 connected to a motor. This rotating pivot 224 and motor are used for rotating the cartridge 50 around the pivot. One or more tubes and/or cones or any other suitable storing means are inserted in the cartridge cylinders 226. In this exemplary embodiment cartridge 50 includes six cylinders 226. Each cylinder 220 can receive one tube or cone. The cartridge 50 is constructed in such a way that the cones and/or tubes are positioned perpendicular to the apparatus cartridge stand 220 and one at a time cone or tube in the cartridge is aligned with the funnel outlet 228 for receiving the mixed and grounded substances. Cone/tube elevation means 222A is used to elevate the cone that is aligned with the funnel 201 which allows the aligned cone/tube to better receive all of the mixed grinded substances that drops from the outlet 228 of funnel 201. Cone/tube elevation means 222B is used for elevating the filled cone/tube in order that the user can be able to remove the filled cone/tube from the cartridge cylinder 226.

The cone/tube elevation means 222A and 222B can be for example a protruded element connected to a spring in order that the protruded element will protrude upwards only when the protruded element is aligned with cylinder 226. Please note, that any other Cone/tube elevation means 222A and 222B known in the art can be used for lifting the cone/tube in the cylinder 226 upwards. Cartridge 50 is configured to rotate around pivot 224, positioned perpendicular to apparatus bottom surface 220. Cones and/or tubes are positioned in even distances from pivot 224 in such a way that each tube or cone can be aligned with the funnel outlet 228 when rotating the cartridge around pivot 224. Whenever cone or a tube is filled with the mixed substances, cartridge 50 rotates to the next cone or tube to be filled with the mixed substances. Cartridge 50 rotates automatically by a predetermined electric signal command sent from the controller 100 that was described previously in FIG. 2. Pivot 224 is actuated by a motor and a controlled driver. Cartridge stand 220 may further includes a vibrating mechanism with a small vibrating motor whose function is to vibrate the cone or tubes in the cylinders when the cone or tube is filled with the grounded and mixed substances for compressing the substances particles in the filled cone or tube.

FIG. 6 also shows grinder 18 having chopping and breaking elements 232 for chopping and breaking the raw substances in one of the two aforementioned compartments. A sensor means 239 is shown schematically in FIG. 6 and is used for identifying if cylinder 226 is empty, that is, cone or tube is not inserted into cylinder 226. The sensor means 239 is also electrically connected to the controller 100 (shown in FIG. 2) for processing the sensor readings in order for example to prevent grounded and mixed substances to fall from funnel 201 when an empty cone or tube is not inserted into cylinder 226. Sensor means 239 can be for example a suitable laser sensor module or infrared sensor module or any other suitable sensor module.

Figure 7:
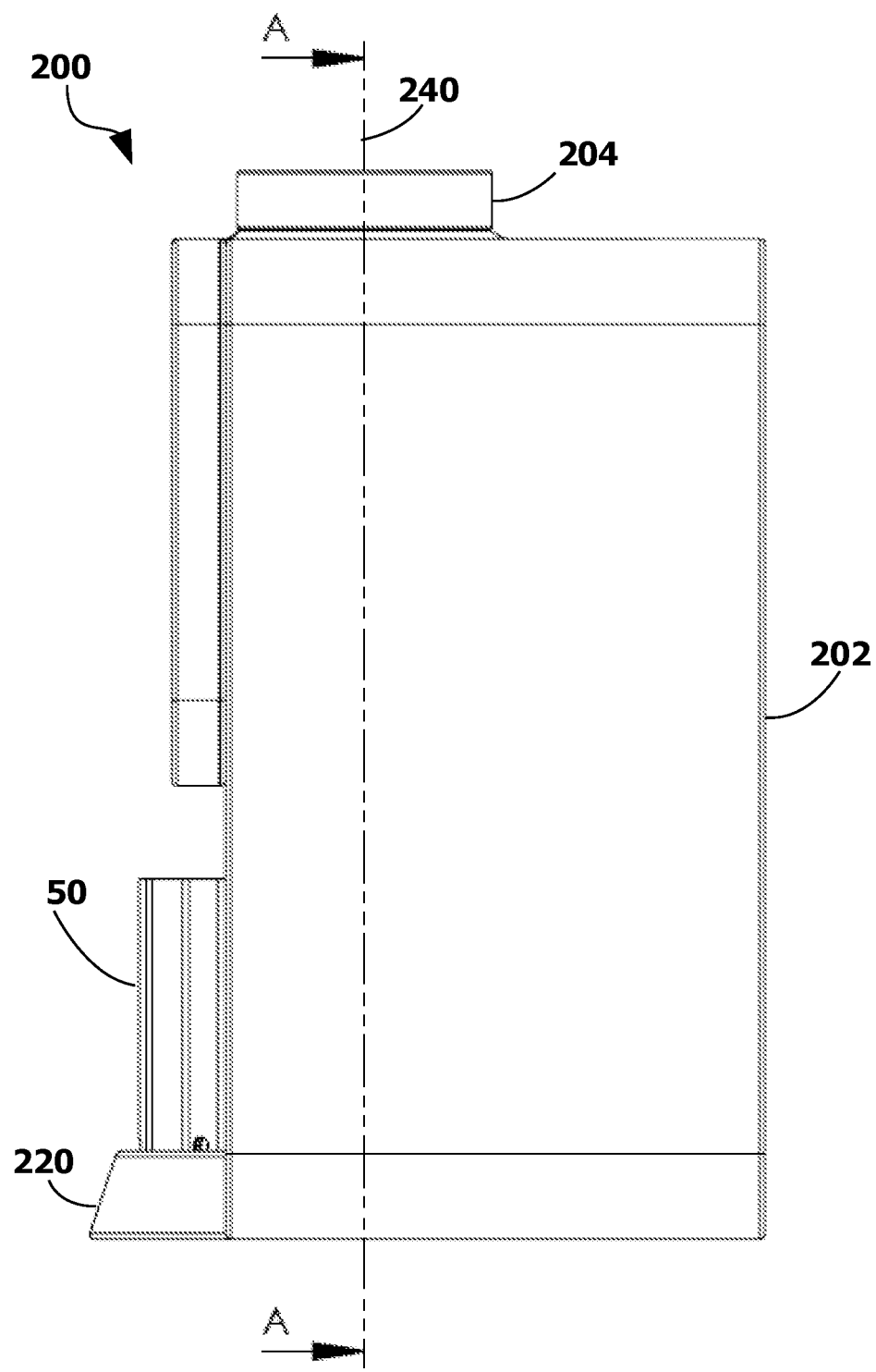
FIG. 7 is a side view of the apparatus for preparing mixed cannabis and tobacco joint as shown in FIG. 4.
Figure 8:
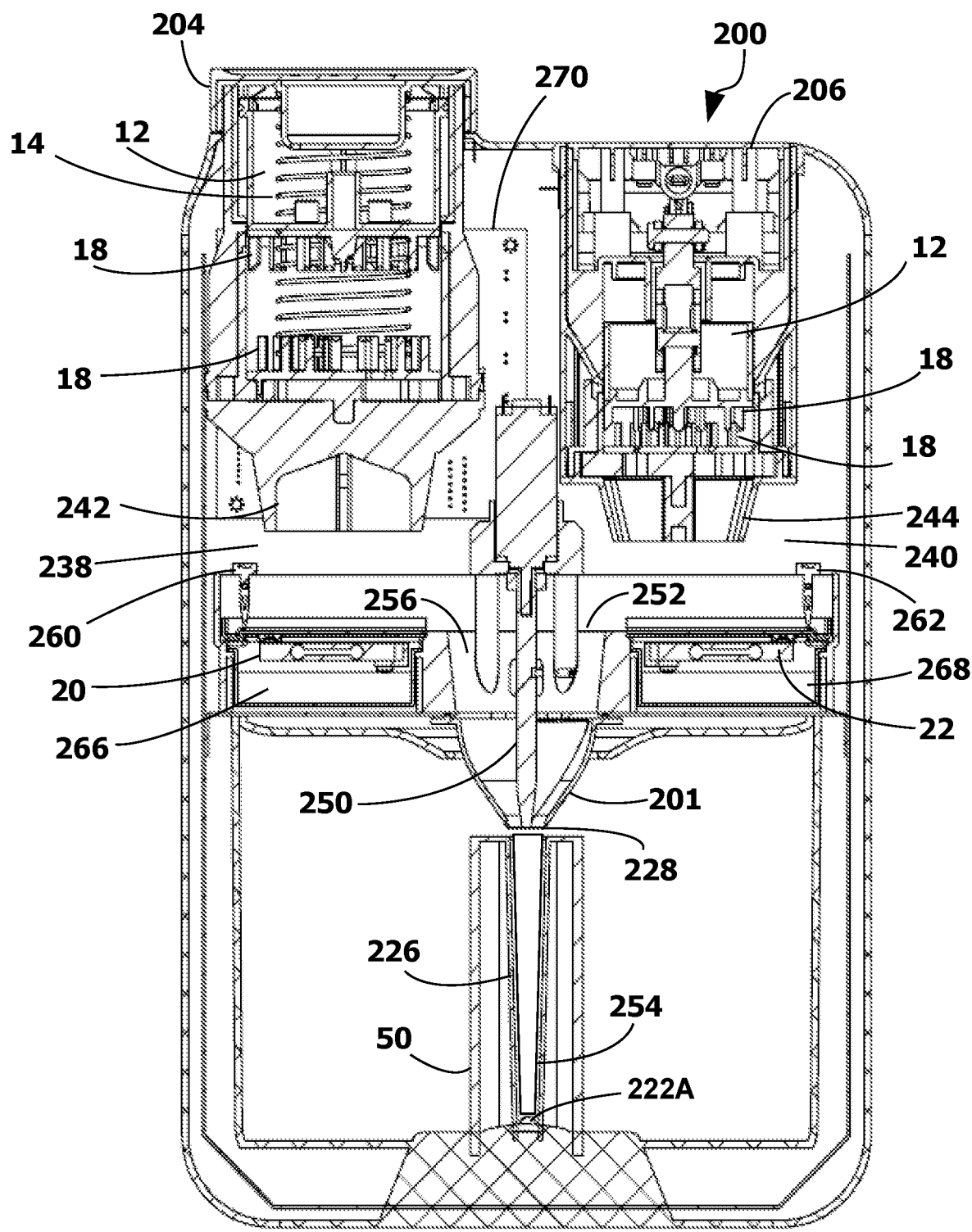
FIG. 8 is a perspective sectional front view of the apparatus for preparing mixed cannabis and tobacco joint as shown in FIG. 4.

Referring to FIGS. 7 and 8, the dashed line 240 is designated for showing the cut of the sectional view of FIG. 8. Apparatus 200 includes compartment 12 and compartment 14. Compartment 12 and 14 may include any suitable compression means 16 for compressing the substances inside compartments 12 and 14. Apparatus 10 further includes one or more grinders 18 typically having chopping and breaking elements for chopping and breaking the raw substances. The grinders 18 are operated by one or more actuators such as but not limited to electric motors which are provided to assist with the grinding operation. Apparatus 10 further includes digital scales 20 and 22. The grinder(s) 18 may further include filters which only the particles of the ground substances which are small enough pass through the filters to grinding chambers 238 and 240. The ground substances pass through outlet of funnels 242 and 244 to the digital scales 20 and 22 respectively. According to the present invention the grinding operation can be operated automatically and for predetermine time thus in associate with digital scale(s) 20 and 22 measurements and controller 100, the apparatus 200 provide mixed cannabis and tobacco substances with predetermined quantity proportion between them. The controller 100 instructs to operate the actuators of the grinders 18 for a predetermine time then the ground substances are measured separately. The measurements reading are sent to the controller 100 for processing the measurement results. According to the measurement results the controller 100 instructs the grinder 18 how long and when to operate in order to get the desired quantity proportion between the substances. Apparatus 200 further includes mixer 250 having a mixer chamber 256 for receiving the weighted tobacco and cannabis substances and mixing them together. Suitable sweeper mechanisms 260 and 262 are provided for sweeping the measured ground substances to mixer chamber 256. The mixed substances are passed through the funnel 201 having an inlet 252 and outlet 228. The funnel 201 is configured for inserting the mixed and grounded tobacco and cannabis substances to an empty cone or tube 254 which is inserted in cylinder 226 and is centrally aligned with the funnel outlet 228. Apparatus 200 further includes two receptacles 266 and 268 that collect the remaining grinded substances that fall from funnels 242 and 244 respectively and not resting on the digital scales 20 and 22 respectively. The parts of the apparatus 200 such as but not limited to the grinders 18 and the compartments 14, 12, 266 and 268 can be removable cleaned and washed. Apparatus 200 further includes a printed circuit 270 that includes the electrical components that are described in FIG. 2 such as but not limited to the power supply circuitry 122, controller 100 and communication unit 120. Apparatus 200 includes actuators for actuating the mixer 250, pivot 224, grinders and sweepers 260, 262.

It should be understood that the above description is merely exemplary and that there are various embodiments of the present invention that may be devised, mutatis mutandis, and that the features described in the above-described embodiments, and those not described herein, may be used separately or in any suitable combination; and the invention can be devised in accordance with embodiments not necessarily described above.

The invention claimed is:

1. An apparatus for automatically preparing a mixture of particles comprising at least two substances initially disposed within first and second compartments, comprising:
   first and second compartments for respectively containing said at least two substances;
   first and second grinders operatively associated respectively with said first and second compartments, wherein each one of said first and second grinders has an inlet and an outlet and a chopping device having breaking elements for chopping and breaking said at least two substances, that pass through said grinder inlets, into ground substances;
   first and second scales operatively associated respectively with said first and second grinders for separately measuring said ground substances that pass through said outlets of said first and second grinders;
   a controller for receiving measurements from said first and second scales and for generating instruction signals to said first and second grinders for grinding said at least two substances so as to define a predetermined mixed proportion between said at least two ground substances as a result of operating said first and second grinders for predetermined periods of time;
   at least one mixer, operatively connected to said controller, for mixing said at least two ground substances together; and
   a receptacle for receiving said predetermined mixed proportion of said two substances.

2. An apparatus according to claim 1, wherein said at least two substances are raw cannabis flowers and raw tobacco.

3. An apparatus according to claim 1, wherein said at least two substances are selected from varieties of marijuana strains.

4. An apparatus according to claim 1, wherein said receptacle is selected from a group comprising rolled paper, a cone, and a tube.

5. An apparatus according to claim 1, wherein said first and second compartments comprise compressors for compressing said at least two substances disposed inside said first and second compartments.

6. An apparatus according to claim 1, wherein the size of at least one of said first and second compartments is intended for predefined small quantities of raw herbal material.

7. An apparatus according to claim 1, wherein at least one of said first and second grinders further comprises a filter through which only the ground substances, being small in size, can pass.

8. An apparatus according to claim 1, wherein at least one of said first and second scales is a digital scale.

9. An apparatus according to claim 1, wherein according to said measurements received from said first and second scales, said controller instructs said first and second grinders when to operate and for how long in order to obtain the desired quantity proportion between said at least two substances.

10. An apparatus according to claim 1, wherein said measurements, received from said first and second scales, are stored in a memory for measurement analysis.

11. An apparatus according to claim 1, wherein said apparatus further comprises a sweeper for sweeping said measured ground substances particles toward said mixer.

12. An apparatus according to claim 4 wherein:
at least one cone/tube is adapted to contain said mixture of particles comprising said at least two substances;
a funnel is attached to a bottom portion of said mixer;
said funnel has an inlet and an outlet and is configured for conducting said mixture of particles comprising said at least two substances into said at least one cone/tube; and
wherein said funnel outlet is aligned with an inlet of said at least one cone/tube.

13. An apparatus according to claim 12, further comprising:
at least one cartridge for carrying a plurality of cones/tubes such that said plurality of cones/tubes are positioned perpendicular to a bottom surface of said apparatus and said plurality of cones/tubes, disposed within said cartridge, can be sequentially aligned with said funnel outlet for receiving said mixed ground substances.

14. An apparatus according to claim 13, wherein said cartridge rotates in response to a signal command sent from said controller.

15. An apparatus according to claim 1, further comprising:
at least one remote digital device
a communication unit which communicates with said at least one remote digital device;
said at least one remote digital device receives and/or sends information from/to said apparatus through said communication unit;
said at least one remote digital device comprises a database and algorithms for analyzing readings from said first and second scales and for providing said remote device with useful information about user consumption habits of said at least two substances based upon information received from said apparatus through said communication unit.

16. An apparatus according to claim 15, wherein said remote device controls said apparatus wirelessly.

17. An apparatus according to claim 1, wherein said apparatus parts can be disassembled for cleaning and replacement purposes.

18. An apparatus according to claim 13, further comprising:
first and second elevational actuators wherein a first one of said elevational actuators is used for elevating one of said plurality of cones that is aligned with said funnel, and wherein a second one of said elevational actuators is used for elevating a filled cone/tube within said cartridge in order to assist a user in removing a filled cone/tube from said cartridge.

19. An apparatus according to claim 13, further comprising:
a vibrating mechanism, comprising a small vibrating motor, for vibrating said cones/tubes disposed within said cartridge when a particular one of said plurality of cones/tubes is filled with ground and mixed substances which are to be compressed within said filled cone/tube.

20. An apparatus according to claim 13, further comprising:
a sensor for determining whether or not said at least one cylinder is empty, that is, whether or not a cone/tube has been inserted into said at least one cylinder.

21. A method for preparing a mixture of particles comprising at least two substances initially disposed within first and second compartments, comprising the steps of:
inserting said at least two substances separately into said first and second compartments;
providing first and second grinders operatively associated respectively with said first and second compartments, wherein each one of said first and second grinders has an inlet and an outlet, and a chopping device having breaking elements for chopping and breaking said at least two substances, that pass through said grinder inlets, into ground substances;
providing first and second scales operatively associated respectively with said first and second grinders for separately measuring said ground substances that pass through said outlets of said first and second grinders;
providing a controller for receiving measurements from said first and second scales and for generating instruction signals to said first and second grinders for grinding said at least two substances so as to define a predetermined mixed proportion between said at least two ground substances as a result of operating said first and second grinders for predetermined periods of time;
providing at least one mixer, operatively connected to said controller, for mixing said at least two ground substances together; and
filling a receptacle with said at least two mixed ground substances.

22. A method according with claim 21, wherein said at least two substances are cannabis and tobacco.

23. A method according with claim 21, wherein said receptacle is selected from a group comprising rolled paper, a cone, and a tube.

24. A method according with claim 21, wherein said at least two substances are raw substances.

25. A method according with claim 22, further comprising the step of:
filtering said ground substances.

* * * * *